United States Patent [19]

Chou

[11] 4,066,754
[45] Jan. 3, 1978

[54] SLOW RELEASE BOLUS
[75] Inventor: Shih-Toon Chou, St. Louis, Mo.
[73] Assignee: Ralston Purina Company, St. Louis, Mo.
[21] Appl. No.: 680,025
[22] Filed: Apr. 26, 1976
[51] Int. Cl.$^2$ .................. A61K 31/635; A61K 31/65; A61K 47/00
[52] U.S. Cl. ................................... 424/229; 424/227; 424/359
[58] Field of Search ...................... 424/359, 227, 229

[56] References Cited

U.S. PATENT DOCUMENTS

| | | | |
|---|---|---|---|
| 2,895,880 | 7/1959 | Rosenthal | 424/359 |
| 3,181,998 | 5/1965 | Kanig | 424/359 |

Primary Examiner—Sam Rosen
Attorney, Agent, or Firm—W. Dennis Drehkoff

[57] ABSTRACT

A composition for slowly releasing a veterinary medicament in a ruminant animal is described. The composition comprises a water-insoluble and water resistant binder a therapeutically active substance and a critical water-insoluble controlled release agent. The process of the invention includes the steps of adding a solution of a water-insoluble binder dissolved in an organic solvent to a mixture of a therapeutically active substance and a water-insoluble dense filler, stirring the mixture until free flowing granules are formed, drying the granules, blending the dried granules with a lubricant and a water insoluble controlled release agent and compressing the mixture into convenient veterinary dosage forms. When the veterinary composition is orally administered to a ruminant animal it remains in the animal's body for a desired period of time and the therapeutically active substance contained therein is released in a predictable and controllable pattern.

29 Claims, No Drawings

SLOW RELEASE BOLUS

BACKGROUND OF THE INVENTION

This invention relates in general to orally administered, slow release compositions and more particularly to a relatively dense sustained release composition for ruminant animals that permits a predicted and controlled release of medicaments and the process for manufacturing the same.

Several sustained release bolus preparations are available to veterinary medical personnel but many do not enjoy widespread commercial use. These sustained release dosage forms are used for oral administration of therapeutic substances to ruminants such as cattle, sheep and goats. The physical shape of these sustained release dosage forms is in the form of a bolus that is dense and heavy enough to be retained in the rumeno-reticular sac for long periods of time while the therapeutically active substance is slowly released by disintegration of the boluses and granules within the rumeno-reticular sac. However, the release of the therapeutically active substance from the bolus is unpredictable and not controllable. A portion of the therapeutically active substance is released in the rumen where it is exposed to ruminal bacteria which can inactivate the therapeutically active substance. Additionally, the microbes in the rumen can also be rendered ineffective and disturb the normal digestive fermentation process in the rumen. This, of course, is undesirable, and there is a definite need for a sustained release bolus to have a predictable and controllable release of a therapeutically active substance so that it is not inactivated in the rumen or disruptive of the normal digestive process in a ruminant.

U.S. Pat. No. 3,056,724 discloses pellets for administration to ruminants which provide biologically active substances to the animal's alimentary tract over extended periods of time. The disclosure states that trace elements in pellet form may stay in the animal for an excess of one year, whereas therapeutic substances, such as sulfonamide or antibiotic medication will last for about three months or so. However, a pellet form for administration of a therapeutically active substance that may be utilized for a short period of time is not disclosed. The need for a slow release short term bolus arises in food producing ruminants, for any medication given to the animal must be clear of its tissues before the animal is slaughtered.

U.S. Pat. No. 3,507,952 describes a bolus containing a therapeutically active substance combined with a filler and a critical lubricant. The bolus supplies the therapeutically active substance to the ruminant for short periods of time in minimal dosage levels. As a practical matter, the bolus has minimal and inadequate effects on acute and chronic diseases of ruminants.

The present invention relates to an improvement in the control of disintegration of veterinary boluses in ruminant animals, with said boluses releasing a therapeutically active substance for a period of up to about 15 days in duration.

We have found that by the process of this invention controlled release veterinary boluses for relatively short term therapeutic effects can be prepared with a vegetable proteinaceous material which has never before been recognized as a critical ingredient in the manufacture of a controlled release composition. This critical ingredient is zein, which possesses unique solubility characteristics significantly different from conventional binding agents and disintegrants. Zein when used in the process of the present invention serves a multiple purpose: a portion of zein is utilized as a controlled release agent which facilitates the gradual breakdown of the bolus to granules in the rumeno reticular sac and zein is also utilized as a granulation binder to (a) protect the active ingredients, such as antibacterials in the granules until they are carried to the intestine where the active ingredient is released; (b) protect the vital essential microorganisms normally responsible for digestive fermentation within the rumen from being adversely affected by the therapeutically active ingredient, particularly, antibacterials, such as sulfonamides and antibiotics. This multiple action of the vegetable proteinaceous material, particularly the action wherein the bolus is broken down into granules, provides for the dispensing of medicaments to ruminants for relatively short periods of time without frequent oral administration of the medicament. The method and composition of this invention therefore obviates the prior art disadvantages of unpredictable release, long term effect, harmful effects on ruminal microorganisms and inadequately maintained blood levels of therapeutically active substances, particularly antibacterials such as sulfonamides, by simplifying the prior art procedure to fill a commercial need for a bolus with a relatively short term effect, for example, up to about 15 days.

SUMMARY OF THE INVENTION

The present invention comprises a composition for releasing a therapeutically active substance or veterinary medicament in ruminant animals in a controlled pattern for a desired period of time. The present invention further comprises a process for making said composition by adding a binder solution to a mixture of a therapeutically active substance and a dense filler, forming granules, drying the granules, blending the dry granules with a water-insoluble controlled release agent and compressing the mixture into veterinary dosage forms convenient for oral administration to ruminant animals.

One of the principal objects of this invention is to provide a sustained release dosage form for ruminant animals and a process for manufacturing the same.

Similarly, it is an object of the present invention to provide a dosage form of the type stated which is capable of being retained in the rumeno-reticular sac of ruminant animals for a known period of time. A further object of the present invention is to provide a sustained release dosage form that is relatively dense and is capable of releasing a therapeutically active substance in a predictable and controllable pattern. An additional object is to provide a water-insoluble and water resistant vegetable proteinaceous material that can be used as a binder and controlled release agent in the composition of the sustained release dosage form. Yet another object is to provide a simple process for making the sustained release veterinary composition, which utilizes readily available materials. These and other objects and advantages will become apparent hereinafter.

DETAILED DISCUSSION

This invention concerns a novel method of preparing a dosage form of medicaments, hormones, vitamins, mineral salts, antibiotics, or anthelmintics for animals, particularly ruminants.

This invention was conceived and developed largely for sulfa drugs, particularly 4,6-dimethyl 2-sulfanilamidopyrimidine (hereinafter referred to as sulfamethazine) because of the special problems encountered with developing a sustained release composition that would provide adequate blood levels of that drug for extended periods of time. Therefore, it will be explained largely with respect to sulfamethazine, and has special application to that drug, although it can be used for other therapeutically active ingredients in the broader aspects of the invention.

A single oral dose of the composition of the present invention allows a slow and continuous release of active ingredients, particularly sulfamethazine, for a period of time up to about 15 days, preferably about 4 to about 15 days. The preferred embodiment of this invention includes the use of an effective amount of a vegetable proteinaceous material as a water insoluble and water resistant binder and control release or disintegrating agent. This vegetable proteinaceous material is zein, a prolamine constituting the principal protein in corn. Zein is obtained by extracting corn gluten with an aqueous solution of isopropanol. The resultant dried extract is a yellowish-grainy powder that is used chiefly in making textile fibers, plastics, printing, varnishes and other coatings, adhesives, sizes and as a binder and enteric coating material for tablet formulations in the pharmaceutical industry. It has unique solubility characteristics in that it does not dissolve in water, or weak alkaline systems. Zein is soluble in aqueous alcohols and low molecular weight organic acids such as acetic, lactic and propionic acids. Additionally, zein is soluble in highly alkaline aqueous systems such as in the duodenum or the proximal section of the small intestine of the ruminant animal, giving it ideal slow release properties.

Zein is multi-functional in the process of the instant invention. It is utilized as a water-insoluble and water resistant binder when mixed with an organic solvent to granulate the powdered ingredients of the composition. Also, powdery zein is used at a critical level to slowly disintegrate the compressed bolus within the ruminant. The use of zein as a granulation binder serves to protect the therapeutically active ingredient by reducing the exposed surface of the ingredient to direct contact with the acidic rumen fluid which often inactivates therapeutically active substances, while at the same time protecting the vital essential microorganisms normally responsible for digestive fermentation within the rumen from being adversely affected by the therapeutically active ingredient. These protective devices insure efficient use of anti-bacterials such as sulfonamides, and antibiotics in ruminants without upsetting the normal functioning of the digestive system.

An effective amount of zein is utilized in the present invention to provide the desired sustained release of a therapeutically active ingredient. However, a total of about 6 to about 35% by weight of zein is preferred in the bolus. About 5 to about 25% by weight of the zein may constitute the binder and about 1.0 to about 10% by weight of the zein may be used as the disintegrating agent.

Zein is used to impart cohesive qualities to the powdery ingredients of the bolus. It imparts a cohesiveness to the formulation which insures free flowing qualities by the formation of granules of desired hardness and size. Zein is the preferable binder to be used in this invention. Other water-insoluble binders known in the art will also function in the present invention such as cellulose esters, preferably ethyl cellulose, but the best results are obtained with zein. Effective amounts of ethyl cellulose, preferably about 2 to 8% by weight, can be used as an alternative binder in the present invention. These amounts appear to release the active ingredient from the granules in the rumen as well as in the small intestine. Ethyl cellulose does not release the therapeutically active substance as rapidly and completely as zein does in the small intestine. If ethyl cellulose is used as a binder, small amounts of the active substance are continuously released throughout the stomach where it can be inactivated by the acidic medium or damage the microorganisms in the rumen. Likewise, conventional or water soluble binders such as starches and gums cause the granules to break up shortly following their introduction to the stomach exposing the active ingredient to acidic rumen fluid and the normal bacterial flora of the rumen.

It is preferable to incorporate the binding agent of the present invention in solution so that all the powders of the composition can be easily and evenly wetted. Preferably, from about 5 to about 25% by weight of the bolus of the water insoluble and water resistant zein granulation binder of the present invention is mixed with a suitable organic solvent to provide a binder solution that will thoroughly wet each of the particles within the mass of powders of the composition. The organic solvent used in combination with the zein is allowed to evaporate after wetting the materials in the composition and can be selected from a group consisting of isopropanol, ethanol, methanol, acetone, furfuryl alcohol, or tetrahydro furfuryl alcohol, or combinations thereof. Preferably, either isopropanol or ethanol is used to make a zein solution containing about 5 to about 50% by weight of zein in the solution.

In an alternate embodiment of this invention, the organic solvent can be admixed to the mixture of the water-insoluble binding agent, filler material and therapeutically active substance until granules are formed. In this procedure an effective amount of organic solvent and waterinsoluble binding agent is utilized to form granules of the therapeutically active substance and filler material.

A dense inert substance may be added to the composition to increase the density in order to assure the bolus to remain in the rumeno-reticular sac. The filler material which may be employed in the process of the instant invention is preferably relatively water insoluble and can be chosen from any well known in the art, such as iron powder, ferric oxide, calcium sulfate, portland cement, plaster of paris, talc and magnesium oxychloride or mixtures thereof. Preferably, the dense filler will be iron powder or talc or a combination of the two. The filler should be present in the composition of the present invention from about 10 to about 95% by weight of the total solids. Preferably, the filler should be present from about 25 to about 60% by weight.

The addition of the proper lubricant is highly desirable in the instant invention for it improves the rate of flow of the bolus granulation, prevents adhesion of the bolus composition to the surface of the dies and punches on the bolus press, reduces interparticle friction and facilitates the ejection of the bolus from the die cavity. The lubricant employed in the composition of the present invention can be any of the more common lubricants known in the art such as, for example, magnesium stearate, sodium stearate, calcium stearate, and stearic acid. The lubricant is present in the composition from about 0.1 to about 0.5% by weight of the total solids.

As indicated heretofore, this invention was developed largely for the sustained release of sulfamethazine in ruminants. However, this invention is useful with any solid medicament or therapeutically active substance which is desired to be provided in sustained release form. The medicament may be a sulfonamide derivative such as sulfamethazine or sulfathiazole, hormones, vitamins, mineral salts such as magnesium carbonate, antibiotics, such as chlortetracycline hydrochloride, and anthelmintics or antibloat agents. The foregoing list is illustrative only and is not intended as limitative on the scope or practice of the invention. The therapeutically active substance should be present in the bolus from about 1% to about 80% by weight.

The novel and critical feature of this invention is the use of zein as a vegetable proteinaceous controlled release or disintegrating agent which is (1) slowly dissolved in rumen fluid and (2) is slowly broken down by microorganisms in the rumen. Substantial disintegration and release of the therapeutically active substance occurs in the highly alkaline medium of the small intestine. The granules of the therapeutically active substance pass through the acidic medium of rumen fluid under the protection of zein to be released in the small intestine substantially intact. The zein not only substantially protects the therapeutically active substance from the acidic conditions in the rumen but also protects the essential microorganisms normally responsible for digestive fermentation within the rumen from being adversely affected by the therapeutically active substance. The binding and protecting functions of the zein may be partially accounted for because of its acid resistant and water insolubility or water resistant nature. A substance is water resistant when it does not absorb water.

A controlled release, timed release or disintegration agent can be defined as a substance or mixture of substances added to a composition to facilitate its breakup or disintegration after administration into an animal. The use of zein in this invention provides for a controlled breakdown and distribution of bolus particles by the rumen fluid and bacteria found in the ruminant. Minute but critical levels of a conventional disintegrant, such as microcrystalline cellulose, can be added to further refine and regulate the rate of bolus disintegration in the rumeno-reticular sac. The effective amounts of powdery zein and microcrystalline cellulose when mixed with all the ingredients of the bolus mixture prior to compression, facilitates timed disintegration of the bolus into granules that continuously flow into successive portions of the digestive tract and are eventually disintegrated to release the therapeutically active ingredient for a continuous absorption of the ingredient for a period of up to 15 days in duration. Disintegrating agents known in the prior art such as corn and potato starch and fibrous material, such as Avicel brand of microcrystalline cellulose, manufactured by the FMC Company, have great affinity for water and swell when moistened and thus facilitate a rapid rupture of the bolus matrix. Therefore, the use of these conventional disintegrating agents alone has not proven to be satisfactory for a sustained release bolus preparation. The water insoluble and water resistant controlled release agent of the instant invention, grainy powdery zein, should be present in effective amounts to provide the desired sustained release properties to the therapeutically active ingredient, but preferably in amounts of about 1.5 to about 10% of the total solids weight and most preferably, about 2 to about 4%. The grainy powdery texture of the zein is noted to physically distinguish it from the zein which is used as a binder when dissolved in an organic solvent. Therefore, when zein is referred to as a binder, it is in solution with the desired organic solvent and when zein is referred to as a disintegrating agent it is in a grainy, powdery form. Indeed, all particles of powdery zein should preferably pass through a 20 mesh screen. Further, a conventional disintegrating agent, preferably microcrystalline cellulose, may be present in amounts ranging from about 0.5 to 1.5% by weight of the bolus in addition to the powdery zein. The desired period of drug release can be adjusted to about 4 to 15 days in duration by regulating the proportion of critical ingredients and powdered zein, and if present in the formulation, the conventional disintegrating agent.

The amount of zein used as the controlled release agent is the determining factor in the rate of release of the therapeutically active substance. However, the effective amount of zein utilized as the controlled release agent depends upon the physical character of the therapeutically active ingredient and/or the filler material. As a general rule, the heavier or more dense the material, the less zein is required. Additionally, there appears to be an inversely proportional relationship between the amount of zein used in the bolus and the rate of bolus disintegration. That is, for a long duration of treatment, a small amount of zein is used as a controlled release agent and for shorter periods of time, larger amounts of zein are required. For example, the treatment or prevention of an acute case of a disease may be necessary for only a short period of time, say about four days. The grainy powdery zein, which is utilized as a controlled release agent in the instant invention, should be present in an amount of about 2 to 10% by weight of the bolus depending upon the density of the filler material and therapeutically active substances. In a chronic disease condition, treatment should be of a longer duration, possibly up to fifteen days requiring about 1 to 4% by weight of the bolus of grainy powdery zein as a controlled release agent. The proportion of other ingredients, such as the therapeutically active substance can be easily determined by a skilled artisan.

In the preferred process of this invention a binder solution of the zein and organic solvent is formed and added to the mixture of therapeutically active substance and filler material. Granules are formed by the mixing of these ingredients. The granulated mixture is allowed to dry, preferably at about 40° C overnight. However, the drying of the granules commences as soon as they are formed for the organic solvent easily evaporates and any method of drying known in the art is suitable. The dried granules may then be passed through a #12 screen, but this is optional. Next, the zein disintegrating agent is added to the mixture and the bolus is formed by conventional means.

Alternate embodiments of the process involve the admixture of the organic solvent to the mixture of water-insoluble binding agent, filler material and therapeutically active substances until granules are formed. Additionally, a conventional disintegrating agent such as microcrystalline cellulose can be added to the mixture of ingredients to form the bolus.

The final product comprises a mixture of a therapeutically active substance, a dense filler, a binder, a lubricant, a critical timed release agent and an optional conventional disintegrant such as microcrystalline cellulose, compressed into a bolus. In the preferred practice of this invention, the solid product will be compressed into a bolus suitable for ingestion by a ruminant, however, the invention is not limited to a bolus shaped dosage form. The product can be compressed if desired, into other shapes such as tablets or spheres. The bolus provides for a sustained release of the therapeutically active substance having a predictable and controllable release pattern. The bolus should weigh from about 2 to about 40 grams and have a density of about 1.4 to 5.5. Preferably, the bolus should weigh from about 5 to about 30 grams and have a density of about 1.5 to 3.0. The density of the product will allow it to remain in the ruminant animal to release the therapeutically active substance for a period of time up to 15 days in a predictable, controllable pattern. The product has advantages over the prior art in that reduced amounts of the therapeutically active substance are required. Additionally, less frequent administrations of the bolus are required thereby reducing labor costs.

A better understanding of the present invention and of its advantages will be had by referring to the following specific examples given by way of illustration.

EXAMPLE 1

An exemplary formulation of the sustained release bolus of the instant invention is shown in the following Table I.

Table I

| Ingredients of Sustained Release Bolus in Grams per Batch | |
| --- | --- |
| Sulfamethazine | 11.0 |
| Iron powder | 80.5 |
| Powdered zein (as 40% solution) | 6.0 |
| Ethanol (70% w/w) | 12.0 |
| Magnesium stearate | 0.5 |
| Powdered zein | 2.0 |

A binder solution is formed by slowly adding the 6.0 grams of zein to 12 ml aqueous ethanol solution (70%), with continuous stirring at room temperature until the zein is dissolved. The sulfamethazine and iron powder are mixed and the binder solution is slowly added and mixed until granules are formed. The granules are dried overnight at about 40° C. The dried granules are passed through a #12 screen and then thoroughly blended with magnesium stearate and powdered zein and compressed into the desired shape boluses. This batch formulation provided 41 boluses with each having an approximate weight of 2.4 grams and a density of 3.6. The zein granulation binder solution binds the mixture of sulfamethazine and iron powder in granular form. The water resistant nature of the zein retains the sulfamethazine in granular form until the zein is dissolved in the small intestine.

EXAMPLE 2

The formulation seen in Example 1 is utilized in this experiment but the amount of zein used in powdery form is varied to 1%, 2% and 3% by weight of the total composition. The 1% zein formulation utilizes 6 grams of zein in the binder solution and 1 gram zein as the timed release agent. The 2% zein formulation comprises the use of 6 grams in the binder solution and 2 grams powdered zein as the timed release agent. The 3% zein formulation comprises the use of 6 grams zein in the binder solution and 3 grams powdered zein as the disintegration or controlled release agent.

Each formulation was orally administered (sulfamethazine 100 mg/lb of body weight) to four sheep (body weight 108–138 lbs) and blood samples were taken at 6, 24, 48, 72 and 96 hours following administration. The average blood level of sulfamethazine in the animals at the various time intervals is seen in Table II.

Table II

| | Hours | | | | | |
| --- | --- | --- | --- | --- | --- | --- |
| | 6 | 24 | 48 | 72 | 96 | |
| Zein 1% | 8 | 13 | 12 | 11 | 16 | mcg/ml |
| Zein 2% | 15 | 36 | 37 | 28 | 20 | mcg/ml |
| Zein 3% | 15 | 69 | 53 | 20 | 7 | mcg/ml |

As can be seen from the above table, zein appears to regulate the rate of sulfamethazine release to a predictable, controllable pattern. The 2% level is particularly ideal for sustained release use.

EXAMPLE 3

Another exemplary formulation of the sustained release bolus of the instant invention is shown in the following Table III.

Table III

| Ingredients of Sustained Release Bolus | |
| --- | --- |
| | Grams/bolus |
| Sulfamethazine | 13.5 |
| Iron powder | 5.08 |
| Powdered zein (40% solution) | 2.19 |
| Isopropanol (70% w/w) | 4.9 |
| Stearic acid | 0.11 |
| Powdered zein | 0.9 |
| Microcrystalline cellulose | 0.22 |

The procedure for making granules was the same as described in Example 1. The dried granules were blended with stearic acid, powdered zein and Avicel brand of microcrystalline cellulose, and compressed into boluses. The finished bolus weighed 22 grams and had a density of 1.6.

EXAMPLE 4

COMPARATIVE BLOOD LEVEL STUDIES OF SULFAMETHAZINE

The formulation shown in Example 3 was used in this experiment and compared with a commercially available bolus identified as Product A. Product A contained sulfamethazine, weighed 35.5 grams and had a density of 1.7. It was administered according to the manufacturer's recommended instructions, i.e., 121 mg. of sulfamethazine per pound of body weight to six calves weighing between 300 and 650 lbs. The product of the instant invention as formulated in Example 3 was administered to a similar group of calves at 122 mg/lb. Blood samples were collected at 24, 48, 72 and 96 hours following administration for sulfonamide blood concentration determination. The minimal therapeutic level of sulfonamide in whole blood, 33.33 mcg/ml (equivalent to 50 mcg/ml in serum where serum constituted approximately ⅔ volume of whole blood), was maintained for an average of 78 hours for the bolus of the present invention in the calves, whereas the corresponding average time for Product A was 58 hours (Table IV).

Additionally, the peak blood level for the bolus of the instant invention was 68 mcg/ml which is substantially greater than the 47 mcg/ml blood level of Product A.

Table IV

| Time (Hours after administration) | 24 | 48 | 72 | 96 | |
|---|---|---|---|---|---|
| Sulfamethazine mcg/ml Blood | 38 | 47 | 33 | 28 | Product A |
| | 42 | 68 | 57 | 33 | Product of Invention |

The economical advantages of utilizing the product of this invention include savings in the amount of drug required for a particular blood level and reducing labor costs for less frequent administrations than the conventional bolus.

EXAMPLE 5

Another exemplary formulation of the sustained release bolus of the instant invention is shown in the following Table V.

Table V

| Ingredients of Sustained Release Bolus | |
|---|---|
| | Grams/bolus |
| Sulfamethazine | 3.03 |
| Iron powder | 3.02 |
| Zein (as 40% solution, w/w) | 0.68 |
| Isopropanol, (70%) | 1.00 |
| Zein (powered) | 0.14 |
| Magnesium stearate | 0.03 |

The bolus was prepared following the procedure described in Example 1, and had a density of 1.7. Sulfamethazine blood level studies were conducted on sheep. Procedures were similar to those of Example 2. Each sheep received 14 boluses for a total of approximately 42 grams of sulfamethazine in the boluses. Blood levels of sulfamethazine were as follows:

| Time (# of days) | 1 | 2 | 3 | 5 | 7 | 9 | 11 | 13 | 15 |
|---|---|---|---|---|---|---|---|---|---|
| Sulfamethazine (mcg/ml)* | 38 | 34 | 25 | 10 | 11 | 6 | 5 | 6 | 3 |

*Each figure represents nine sheep.

High levels of sulfamethazine are released for the first four to six days to achieve its characteristic therapeutic effect before decreasing.

EXAMPLE 6

INGREDIENTS OF SUSTAINED RELEASE BOLUS COMPOSITION

| | Grams/bolus |
|---|---|
| Sulfathiazole | 11.66 |
| Iron powder | 5.83 |
| Talc | 1.46 |
| Zein (as 40% solution) | 1.97 |
| Isopropanol (70%) | 2.95 |
| Zein (powdered) | 0.88 |
| Microcrystalline cellulose | 0.19 |
| Magnesium stearate | 0.11 |

A binder solution is formed by slowly adding 2.5 grams of zein to 3.2 grams aqueous isopropanol (70%), with continuous stirring at room temperature until the zein is dissolved. The sulfathiazole, iron powder, and talc are mixed and the binder solution is slowly added until granules are formed. The granules are dried overnight at about 40° C. The dried granules are screened and then thoroughly blended with magnesium stearate, powdered zein, and microcrystalline cellulose and compressed into the desired size and shape bolus. The finished bolus had a density of 1.8.

EXAMPLE 7

COMPARATIVE BLOOD LEVEL STUDIES OF SULFATHIAZOLE

The formulation of Example 6 was used in this experiment and administered to six calves having body weights between 300 and 650 lbs. The procedure was similar to the one practiced in Example 4 for blood samples were collected at 6, 12, 24, 48, 72 and 96 hours following ingestion of the sulfathiazole. The dose of 303 mg/lb of body weight sulfathiazole was orally administered to the 6 calves and blood level results were as follows:

| Hours | 6 | 12 | 24 | 48 | 72 | 96 |
|---|---|---|---|---|---|---|
| Sulfathiazole (mcg/ml) | 6.5 | 10.4 | 29 | 28.3 | 14.5 | 5.9 |

The minimum effective therapeutic level of sulfathiazole is 14 mcg/ml. When the foregoing dosage and results are compared with conventional procedures for administering oral doses of sulfathiazole to cattle found on page 489 of *Veterinary Pharmacology and Therapeutics* by L. Meyer Jones, Iowa State University Press, 1965, a marked improvement is indicated by the present invention. Using conventional procedures, a much higher dose, i.e., 349 mg/lb of body weight, is required to produce results similar to those of the present invention foregoingly described.

From the foregoing, it is readily apparent that the release characteristics of the product of this invention are such that sulfonamide levels in blood plasma are maintained over a considerable period of time with a reduced amount of therapeutically active substance.

EXAMPLE 8

INGREDIENTS OF SUSTAINED RELEASE BOLUS COMPOSITION

| | Grams/bolus |
|---|---|
| Chlortetracycline hydrochloride | 2.69 |
| Iron powder | 16.06 |
| Talc | 5.35 |
| Zein (as 40% solution) | 2.43 |
| Isopropanol (70%) | 3.65 |
| Zein (powdered) | 0.54 |
| Microcrystalline cellulose | 0.11 |
| Magnesium stearate | 0.07 |

Chlortetracycline and iron powder are mixed and the binder solution is prepared and added as described in Example 6. The dried granules are thoroughly blended with magnesium stearate, powdered zein, and microcrystalline cellulose and compressed into desired shape and size bolus. The finished bolus had a density of 2.9.

EXAMPLE 9

INGREDIENTS OF SUSTAINED RELEASE BOLUS COMPOSITION

| | Grams/bolus |
|---|---|
| Magnesium carbonate | 5.43 |
| Iron powder | 2.72 |
| Zein (as 40% solution) | 2.81 |
| Isopropanol (70%) | 4.22 |
| Zein (powdered) | 0.46 |
| Microcrystalline cellulose | 0.10 |

| | Grams/bolus |
|---|---|
| Magnesium stearate | 0.06 |

Magnesium carbonate and iron powder are mixed and the binder solution is prepared and added as described in example 6. The dried granules are thoroughly blended with magnesium stearate, powdered zein, and microcrystalline cellulose and compressed into desired shape and size bolus. The finished bolus had a density of 1.9.

The foregoing examples are merely illustrative of the instant invention and it will be understood that various other changes in the details, materials or steps which have been described may be made without departing from the spirit of the instant disclosure, and such changes or other modifications are intended to be included within the scope of the instant disclosure and appended claims.

What is claimed is:

1. An improved method of preparing a sustained release veterinary bolus for ruminant animals having a therapeutically active substance, filler material, binder and lubricant wherein the improvement comprises forming the binder by combining an effective amount of zein and an organic solvent, mixing the binder with the therapeutically active substance and filler material to granulate the mixture, drying the mixture, adding a lubricant, blending the dried mixture with an effective amount of zein to insure sustained release of the therapeutically active substance and forming a bolus of sufficient density that will remain in a ruminant animal to release the therapeutically active substance for a period of time up to 15 days in a predictable, controllable pattern.

2. The method of claim 1 wherein about 6 to about 35% by weight of zein is utilized in the bolus.

3. The method of claim 1 wherein about 5 to about 25% by weight of zein is utilized as a binder.

4. The method of claim 1 wherein about 1 to 10% by weight of zein is utilized as a disintegrating agent.

5. The method of claim 1 wherein the therapeutically active substance is sulfamethazine.

6. The method of claim 1 wherein the bolus has a density of about 1.4 to 5.5.

7. An improved method of preparing a sustained release veterinary bolus for ruminant animals comprising:
    forming a binder solution by mixing about 5 to 25% by weight of the bolus of a binder material with an organic solvent,
    mixing about 1 to about 80% by weight of a therapeutically active substance with about 10 to about 95% by weight of a filler material;
    combining and mixing the binder solution and mixture of therapeutically active substance and filler material to granulate the mixture;
    drying the mixture;
    adding about 0.1 to about 0.5% by weight of a lubricant to the mixture;
    mixing in about 1 to about 10% by weight of a zein disintegrating agent to the mixture and forming a bolus that can be orally administered to ruminant animals to release the therapeutically active substance for a period of time up to 15 days.

8. The method of claim 7 wherein the binder material is zein.

9. The method of claim 7 wherein the binder material is ethyl cellulose.

10. The method of claim 9 wherein a binder solution is formed by mixing about 2 to about 8% by weight of the bolus of ethyl cellulose with an organic solvent.

11. The method of claim 7 wherein the total amount of zein is about 6 to about 35% by weight.

12. The method of claim 7 wherein the amount of zein utilized as a binder is about 5 to about 25% by weight.

13. The method of claim 7 wherein the zein utilized as a disintegrating agent is in the powdery form.

14. The method of claim 7 wherein the therapeutically active substance is selected from the group consisting of sulfonamides, antibiotics, hormones, vitamins, minerals, anthelmintics and anti-bloat agents.

15. The method of claim 7 wherein the organic solvent is selected from the group consisting of isopropanol, ethanol, methanol, acetone, furfuryl, tetrahydro furfuryl alcohol and combinations thereof.

16. The method of claim 7 wherein the filler material is selected from the group consisting of iron powder, ferric oxide, calcium sulfate, portland cement, plaster of paris, talc, magnesium oxychloride and mixtures thereof.

17. The method of claim 7 wherein the lubricant is selected from the group consisting of magnesium stearate, sodium stearate, calcium stearate and stearic acid.

18. The method of claim 7 wherein the disintegrating agent is a combination of microcrystalline cellulose and powdery zein.

19. The method of claim 18 wherein about 0.5 to about 1.5% by weight microcrystalline cellulose is combined with powdery zein.

20. A solid, sustained release veterinary bolus for ruminant animals comprising (1) from about 1 to about 80% by weight of a therapeutically active substance, (2) from about 10 to about 95% by weight of a filler material, (3) from about 0.1 to about 0.5% by weight of a lubricant and (4) from about 6 to about 35% by weight of zein, said veterinary bolus being characterized by containing a binder comprising about 5 to about 25% by weight of zein of foregoing step 4 and a disintegrating agent comprising from about 1 to about 10% by weight of zein.

21. The veterinary bolus of claim 20 wherein the therapeutically active substance is released in ruminant animals for a period of time up to 15 days in a predictable controllable pattern.

22. The veterinary bolus of claim 20 wherein the density of the bolus is about 1.4 to 5.5.

23. The veterinary bolus of claim 20 wherein the weight of the bolus is from about 2 to about 40 grams.

24. The veterinary bolus of claim 20 wherein the therapeutically active substance is sulfamethazine.

25. The veterinary bolus of claim 20 wherein the therapeutically active substance is sulfathiazole.

26. A solid sustained release veterinary bolus for ruminant animals comprising a therapeutically active substance, filler material, binder, lubricant and disintegrating agent with an effective amount of zein utilized in said binder and disintegrating agent to provide sustained release of said therapeutically active substance for a period of time up to 15 days in a predictable controllable pattern while simultaneously protecting the essential microorganisms normally responsible for digestive fermentation within said ruminant animal from being adversely affected by said therapeutically active substance.

27. The veterinary bolus of claim 26 wherein the amount of zein is about 6 to about 35% by weight.

28. The veterinary bolus of claim 26 wherein the amount of zein utilized as a binder is about 5 to about 25% by weight.

29. The veterinary bolus of claim 26 wherein the amount of zein utilized as a disintegrating agent is about 1 to about 10% by weight.

* * * * *